United States Patent [19]

Ito et al.

[11] 4,326,022
[45] Apr. 20, 1982

[54] PHOTOGRAPHIC MATERIAL CONTAINING A HIGH BOILING SOLVENT

[75] Inventors: Kenji Ito; Katsumi Matsuura; Hiroshi Sugita; Toshihiko Kimura; Hideaki Arai, all of Hino, Japan

[73] Assignee: Konishiroku Photo Industry Co., Ltd., Tokyo, Japan

[21] Appl. No.: 211,893

[22] Filed: Dec. 1, 1980

[30] Foreign Application Priority Data

Dec. 7, 1979 [JP] Japan .................................. 54-158113

[51] Int. Cl.³ ................................................ G03C 1/10
[52] U.S. Cl. ...................... 430/546; 430/554; 430/512; 430/555; 430/544; 430/551; 430/601; 430/610
[58] Field of Search .............. 430/546, 544, 377, 512, 430/493, 601, 610, 554, 555

[56] References Cited

U.S. PATENT DOCUMENTS 3,544,336 12/1970 Milton ................................. 430/610
3,676,137 7/1972 Mizuki et al. ...................... 430/546
4,217,410 8/1980 Nakamura et al. ................ 430/546
4,278,757 7/1981 Mukonoki et al. ................ 430/512

*Primary Examiner*—Mary F. Downey
*Attorney, Agent, or Firm*—Linda G. Bierman; Jordan B. Bierman

[57] ABSTRACT

A high boiling solvent useful in silver halide materials is described by the following general formula:

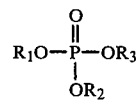

wherein $R_1$ represents an alkyl radical, and each of $R_2$ and $R_3$ represent an aryl radical.

1 Claim, No Drawings

PHOTOGRAPHIC MATERIAL CONTAINING A HIGH BOILING SOLVENT

The present invention relates to a photographic material having a hydrophilic colloidal layer into which oil-soluble substances are incorporated by the use of a high boiling solvent, particularly the oil soluble substance is dissolved in the high boiling solvent and dispersed in the photographic material.

In the manufacturing process of a photographic material, various photographic additives are added to a hydrophilic colloidal liquid for the formation of the component layers of the photographic material. As oil-soluble photographic additives there may be cited, as typical ones, couplers, DIR compounds, ultraviolet absorbing agents, anti-photodiscoloration agents, anti-color stain agents, etc. As one of the methods for incorporating these oil-soluble photographic additives into the component layers of a photographic material, there is known a procedure for dispersedly incorporating into the layer the oil-soluble photographic additive contained as a solute in minute drops, i.e., in the form of particles which comprise a water nonmiscible organic solvent wherein the oil-soluble photographic additive is dissolved. Organic solvents to be used for this purpose are desired to meet the following requirements: The solvents shall be miscible with oil-soluble photographic additives, preferably, they shall substantially dissolve oil-soluble photographic additives, shall have permeability into developing solutions, shall not cause cristallization, deposition and aggregation of the oil-soluble photographic additives contained, shall always disperse stably the liquid particles, shall have as much close refractive index as possible to that of the hydrophilic colloidal binder with them dispersed therein, and shall not soften nor weaken the layer wherein they are dispersedly incorporated, nor deteriorate the physical characteristics of the layer.

There have heretofore been known various organic solvents for use in dispersedly incorporating oil-soluble photographic additives in the form of minute drops, such as described in U.S. Pat. Nos. 2,322,027, 3,554,755, and Japanese Patent Publication 48-32727. For example, there may be cited, as typical examples, the respective phthalates of methyl, ethyl, butyl, benzyl, nonyl and decyl; the respective benzoates of benzyl, butyl-o-methoxy, and n-hexyl; triphenyl phosphate, tricresyl phosphate, tri(2-ethyl-hexyl) phosphate, p-toluensulfonyldimethylamide, benzophenone, acetophenone, tetrahydrofurfuryl succinate, ethyl succinate, ethanol amine, etc.

However, all the oil-soluble photographic additives are not necessarily excellent in the solubility in these high boiling organic solvents. For example, some additives, when dispersed with the use of these high boiling organic solvents, are poor in the dispersive stability, and when dispersed with emulsification by means of a colloid mill of a homoblender; during the lapse of time after the addition of them to gelatin solutions; and during the process of either coating or drying, sometimes may cause deposition of aggregation of their crystals, resulting in uneven coatings or the deterioration of resulting images. And high boiling organic solvents that are capable of fully dissolving couplers, ultraviolet absorbing agents, etc., do not necessarily have good dispersive stability; among the high boiling organic solvents which have heretofore been employed there are some highly excellent in the dissolvability but poor in the dispersive stability, which sometimes cause deposition or aggregation of their crystals during the foregoing either process of the manufacture.

On the other hand, there are also many solvents which, although satisfying the dispersive stability, exert bad influence upon couplers and other additives, and badly deteriorate the natural preservabilities of photographic materials, for example silver halide photographic material and of the dye image after the color development.

Further, in recent years, due to the trends of rapid processings at high temperatures as well as the strict control of photographic processings under antipollution regulations, there are many cases where high boiling organic solvents that have been conventionally used are unable to make couplers function well as color formers.

Especially, some 5-pyrazolone magenta couplers, with the use of conventional high boiling organic solvents, are hardly to perform their satisfactory color development.

It is an object of the present invention to provide a high boiling organic solvent for a hydrophobic substance, especially a photographic additive. The other object is to provide a photographic material having a hydrophilic colloidal layer, into which oil-soluble photographic additive is uniformly, stably and dispersedly incorporated, and which is improved in the uniformity of coating.

Another object of the present invention is to provide a silver halide photosensitive material which is improved in the color formation by couplers without causing any fog and in the preservation of the resulting color image.

The high boiling solvent used in the present invention is represented by the formula

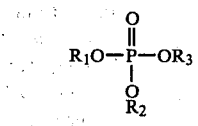

Formula [I]

wherein $R_1$ is a substituted or unsubstituted alkyl, $R_2$ and $R_3$ each is a substituted or unsubstituted aryl, both of which may be either the same or different.

At least one of the compounds represented by the above formula is used to dissolve ultraviolet absorbing agents or other oil-soluble photographic additives, and the resulting solution is added to a hydrophilic colloidal liquid to be dispersedly incorporated thereinto. The thus obtained photographic material is provided with stable dispersion of additives, is free from unevenness of coating, and will not bring about deterioration of the resulting image. Further, when such a material as hereby produced is employed as a silver halide color photographic material, the dye obtained in a color development process will have a sufficient density.

Further, whereas many among the conventionally used high boiling organic solvents deteriorate the resistances of the dye image obtained by color development to light, heat and humidity, the high boiling organic solvents used in the present invention are found out to have a remarkable effect to improve the foregoing resistances.

The high boiling organic solvents represented by Formula [I] used in the present invention enable yellow, cyan and magenta couplers to give their sufficient color formation, and particularly are found out to enable also the sufficient color formation of the 5-pyrazolone magenta couplers having the following Formula [II] or [III], which have heretofore hardly given sufficient color formation with conventional high boiling organic solvents. In the case of the couplers having Formula [III] (multi-pyrazolone type couplers), it is of deep significance that their sufficient color formation have been attained making the most of their intrinsic formalin-resistance.

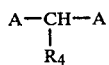
Formula [II]

wherein A represents the residue of a 5-pyrazolone magenta coupler, and $R_4$ represents hydrogen atom or a monovalent organic radical.

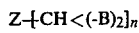
[III]

wherein B represents the residue of a 5-pyrazolone compound the one hydrogen atom at the 4th position of which is removed, n is an integer of 2 or more; when n is 2, Z represents a mere bond or a divalent organic radical, while when n is an integer of 3 and more, Z represents an n-valent organic radical.

The following is the further detailed description of the compound represented by the Formula [I]: $R_1$ should preferably be a straight or branched chain alkyl group of from 1 to 20 (more preferably 4 to 8) carbon atoms, which may be substituted by, for example, halogen, aryl radical, alkyl (or aryl) oxy radical, alkyl (or aryl) oxycabonyl radical, alkyl (or aryl) carbonyl radical, alkyl (or aryl) carbonyloxy radical, alkyl (or aryl) carbamoyl radical, alkyl (or aryl) carbonylamino radical, alkylsulfonyl radical, alkylsulfonamide radical, alkylsulfamoyl radical, etc. The aryl group for $R_2$ or $R_3$ should preferably be, for example, phenyl and naphthyl radicals, which may be substituted with halogen, alkyl radical, alkyloxy radical, alkylcarbonyl radical, alkylcarbonyloxy radical, alkyloxycarbonyl radical, alkylcarbamoyl radical, alkylcarbonylamino radical, etc.

Further concrete examples of Formula [I] are cited below.

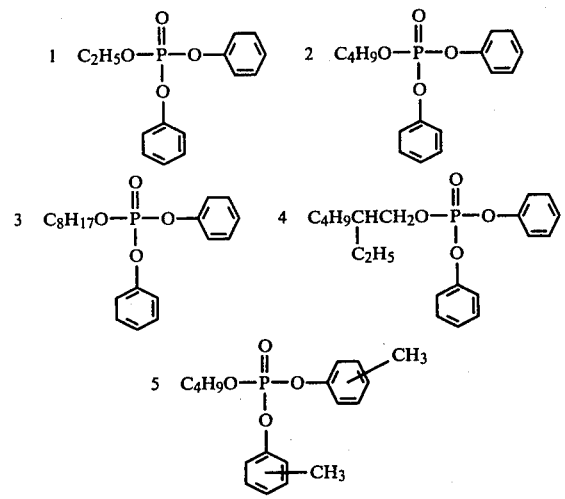

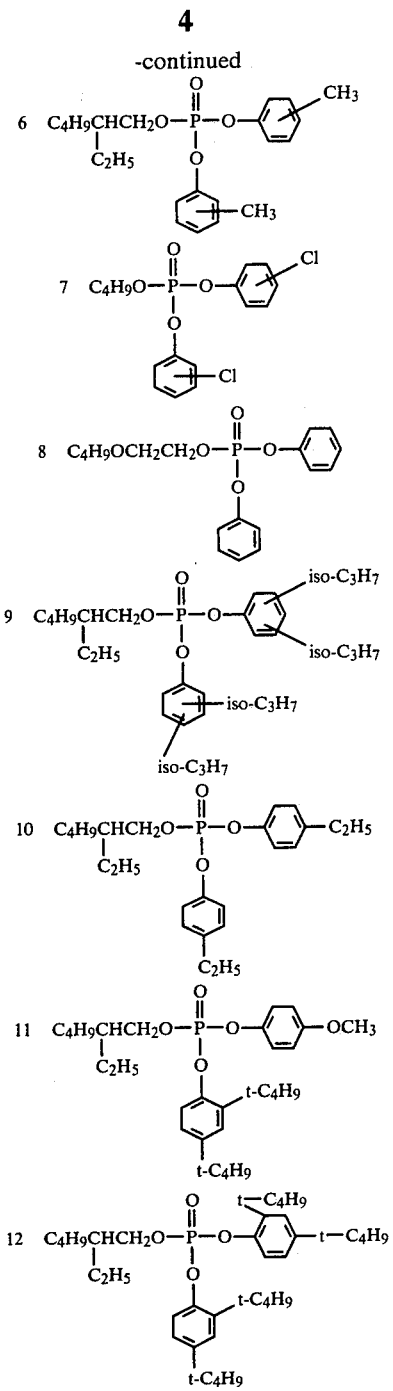

These high boiling solvents of the present invention can be synthesized by such methods as described in U.S. Pat. Nos. 2,596,140 and 2,557,089, British Pat. Nos. 656,471, 734,764, 734,765 or 734,768, or "Kobunshi Kagaku" (Polymer Chemistry) 9 391 (1952).

Procedures for synthesizing the foregoing exemplified compounds preferredly used in the present invention are described below:

Synthesis Example (1) The synthesis of mono-2-ethylhexyldiphenyl phosphate: To 460 g of phosphorus oxychloride put into a 2 liter four-necked flask with cooling by iced water, while stirring, were added dropwise spending the period of an hour and ten minutes 402 g (3.09 M) of 2-ethylhexanol at the temperature of 10° C. And the mixture, with continued stirring, was heated slowly up to 50° C. spending 5 hours and a half, and was then kept at the same temperature for two hours, during which the inside of the flask was slowly decompressed, and finally decompressed down to 200 mmHg to remove the hydrochloric acid gas produced thereinside. When the hydrochloric acid gas was no longer produced, 750 g of mono-2-ethylhexylphosphoryldichloride were obtained (yield: 99.7%).

Subsequently, 400 g (4.25 M) of phenol were added to an equimolar quantity of 40% aqueous sodium hydroxide solution, and to the mixed liquid were added 2,400 ml of m-xylene. The mixture was refluxed with heating and dehydrated, thus producing a sodium phenolate with m-xylene as a dispersion medium. To the obtained product, with cooling and stirring, were added at 20° C. 505 g (about 2 M) of the earlier obtained mono-2-ethyl-hexylphosphoryldichloride spending an hour, and the mixture was further stirred for an hour at the same temperature, for two hours at 20°-30° C., for an hour at 30° C., and for two hours at 40° C. After completion of the reaction, the product was washed to remove the formed sodium chloride therefrom, and was further washed with 3% aqueous sodium hydroxide solution, and then with water, thus yielding a light yellow oily product. The thus obtained product was heated under reduced pressure to remove the m-xylene, and thereafter the residue was distilled under reduced pressure thereby to produce 653 g (yield: 85%) of mono-2-ethyl-hexyldiphenyl phosphate whose B.P. is 190°-195° C./1.0 mmHg. (2) The synthesis of monobutylcresyl: In the same manner as in the synthesis of the mono-2-ethyl-hexyldiphenyl phosphate in (1), to 1086 g (7.07 M) of phosphorus oxychloride were added dropwise 518 g (7 M) of n-butanol at $-1°$ C. to 0° C., spending the period of two hours and 50 minutes, and thereafter slowly raising the temperature up to 40° C., spending 6 hours, during which the pressure inside the flask was slowly reduced down to 200 mmHg thereby to remove the formed hydrochloric acid gas, thus yielding 1341 g (yield: 99.5%) of monobutylphosphoryl dichloride.

Subsequently, 910 g (8.4 M) of cresol and an equimolar quantity of aqueous sodium hydroxide solution were dispersed into 4,000 cc of xylene to produce sodium cresolate (8.4 M), to which were added with stirring the foregoing product, 766 g (4 M) of mono-n-butylphosphoryl dichloride at 20° C., spending the period of an hour and 45 minutes. With further continued stirring the reaction took place for 30 minutes at 20°-30° C., and for an hour at 30° C. The thus obtained reactant was washed, then distilled, whereby 1169 g (yield: 83%) of a monobutyldicresyl phosphate were obtained, B.P. 186-196 C/1.0 mmHg.

In order to disperse oil-soluble photographic additives using the high boiling solvents of the present invention, the former should be dissolved in the latter, and the resulting solution is emulsified and dispersed by means of a colloid mill or a homoblender in an aqueous hydrophilic colloidal solution such as a gelatin solution in the presence of e.g., an anionic surface active agent such as alkylbenzenesulfonic acid, nonionic surface active agent such as saponin, kationic surface active agent such as a quarternary ammonium salt of alkylamines, and thereafter the dispersed product is added to and uniformly dispersed into an aqueous hydrophilic protective colloidal solution for the formation of layer such as a gelatin silver halide emulsion layer or an auxiliary layer (e.g., an interlayer, anti-halation layer, protective layer, etc.). Or, otherwise, a solution of oil-soluble photographic additives dissolved in the high boiling organic solvent of the present invention is also allowed to be directly added to be emulsified and dispersed into a coating liquid for the formation of the component of a photographic material. In the present invention, the dispersion of oil-soluble photographic additives can be fully achieved by using only the high boiling organic solvents comprising the compounds having Formula [I], but may also be achieved by using them in combination with other known high boiling solvents. If necessary, some low boiling organic solvents are also allowed to be used as auxiliary solvents. The low boiling solvents usable in combination include what are described in U.S. Pat. Nos. 2,801,170, 2,801,171, 2,949,360, etc., form which there may be cited, for example, methylisobutylketone, β-ethoxyethyl acetate, methoxytriglycol acetate, acetone, methylacetone, methanol, ethanol, acetonitrile, dioxane, dimethylformamide, dimethylsulfoxide, ethyl acetate, butyl acetate, isopropyl acetate, butanol, chloroform, cyclohexane, cyclohexanol, alcohol fluoride, etc.

Usable quantities of the high boiling organic solvents of the present invention may be arbitrarily selected suitably for couplers, ultraviolet absorbing agents and other oil-soluble photographic additives, respectively, but when used in excessive amounts; e.g., excessive amounts of the organic solvent applied to the upper emulsion layer and/or ultraviolet absorbing layer, etc. of a multilayered silver halide color photosensitive material may result in not only lowering the developability of the lower emulsion layer but deteriorating the physical characteristics of the emulsion layers or gelatin layer containing the high boiling organic solvents, so that it is preferred that the organic solvent be substantially used within the range of from 0.1 to 8.0 parts by weight to 1 part of the respective oil-soluble photographic additives used.

The hydrophilic colloidal liquid for the formation of the component layer into which oil-soluble photographic additives are dispersedly incorporated is coated on an appropriate support such as plastic film, resin-coated paper, baryta paper, etc., and is then dried, whereby a photographic material is produced.

The most typical silver halide emulsion for use in practicing the present invention is usually a gelatin-silver halide emulsion.

The couplers used in the present invention include all known photographic color formers. Among them, preferred ones are, e.g., α-benzoylacetanilide series yellow couplers, α-pivaloylacetanilide series yellow couplers, 5-pyrazolone series magenta couplers, pyrazolinobenzimidazol series magenta couplers, phenol series cyan couplers, and naphthol series cyan couplers.

The α-acylacetamide yellow color formers used in the present invention may be synthesized in accordance with the procedures described in e.g., West German Patents DEOS 2,057,941 and 2,163,812, Japanese Patent L-O-P Publications 47-26133 and 48-29432, U.S. Pat. Nos. 3,227,550, 2,875,057 and 3,265,506, Japanese Patent L-O-P Publications 48-66834, 48-66835, 48-94432, 49-1229, 49-10736, 50-34232, 50-65231, 50-117423, 51-3631 and 51-50734, etc. The α-acylacetamide yellow couplers may be incorporated singly or in a mixture of two or more kinds thereof into a silver halide emulsion layer. The quantity to be incorporated should be 5-30 mols per mol of blue-sensitive silver halide.

These cyan color formers used in the present invention may be synthesized in accordance with the procedures described in, e.g., British Pat. No. 1,084,480, Japanese Patent L-O-P Publications 50-117422, 50-10135, 51-37647, 50-25228 and 50-130441. These cyan color formers may be incorporated into a silver halide emulsion singly or in a mixture of two or more kinds thereof, or otherwise in a mixture with one that is substituted at the active site thereof by arylazo, i.e., the so-called colored coupler as is described in U.S. Pat. No. 3,034,892. The quantity to be incorporated should be 5–30 mols per mol of a red-sensitive silver halide, and the incorporation is to be performed in an ordinary manner.

The following are examples of the magenta color formers for use in the present invention, but are of course not limited thereto.

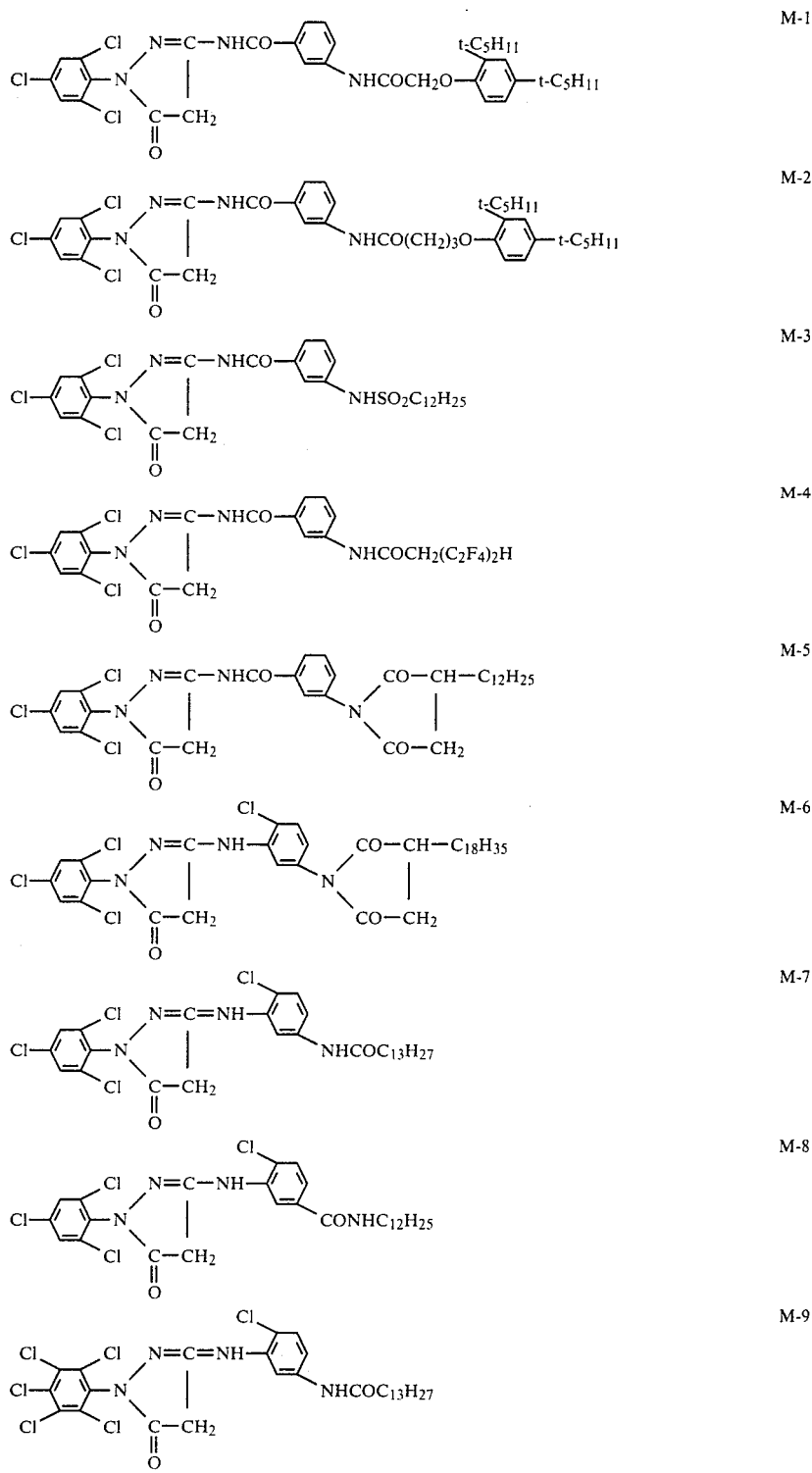

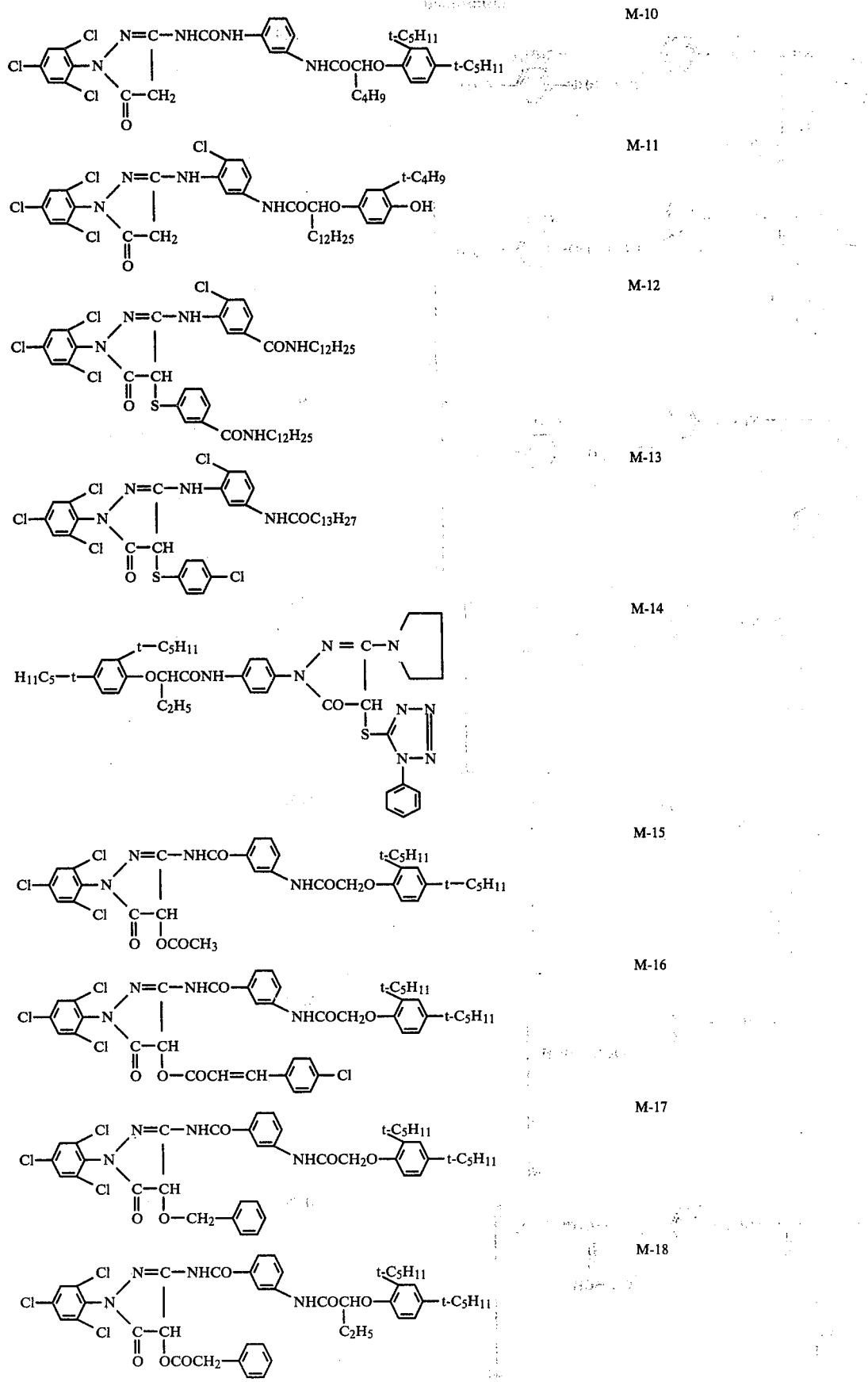

-continued
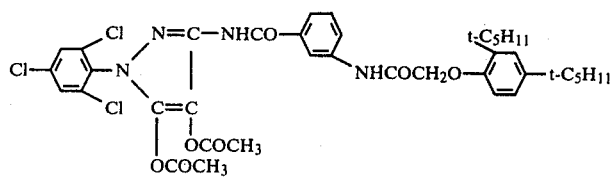
M-19
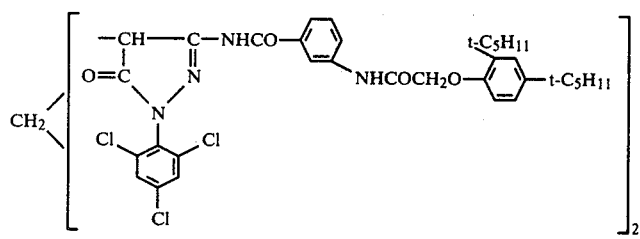
M-20
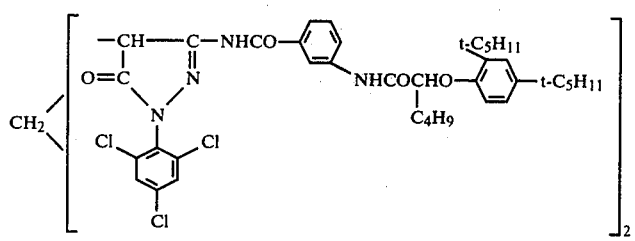
M-21
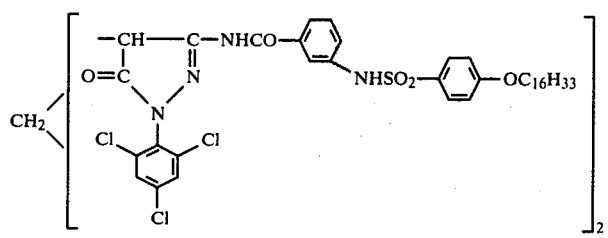
M-22
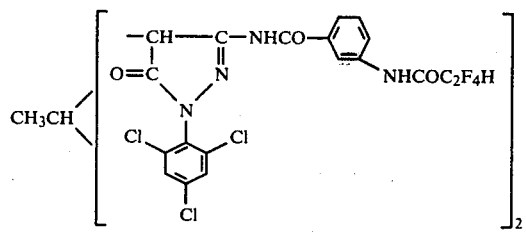
M-23
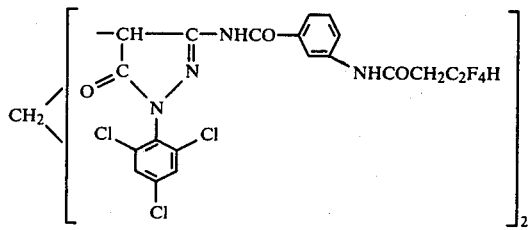
M-24
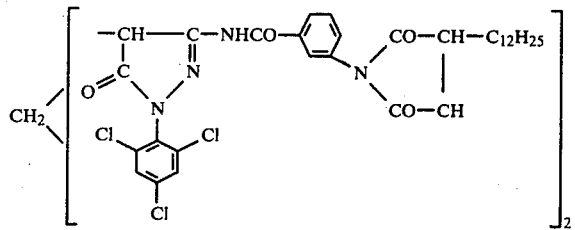
M-25

-continued
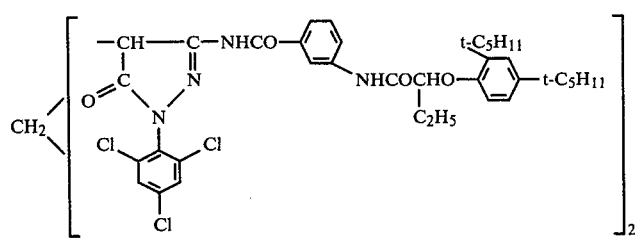 M-26
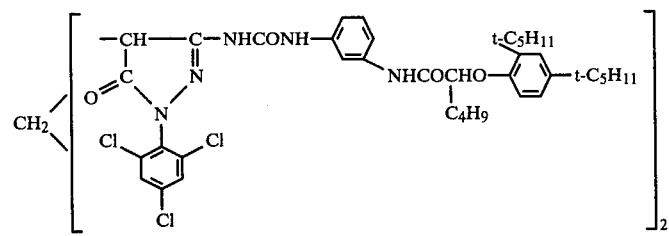 M-27
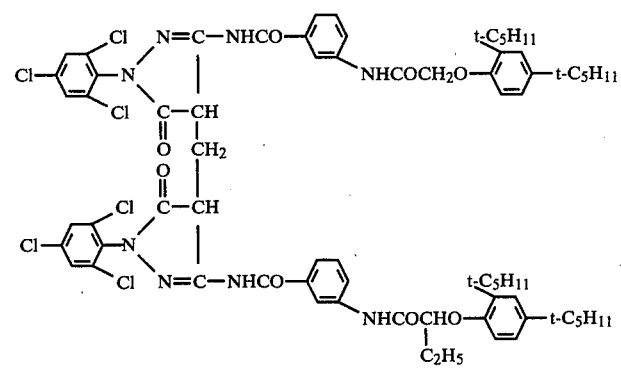 M-28
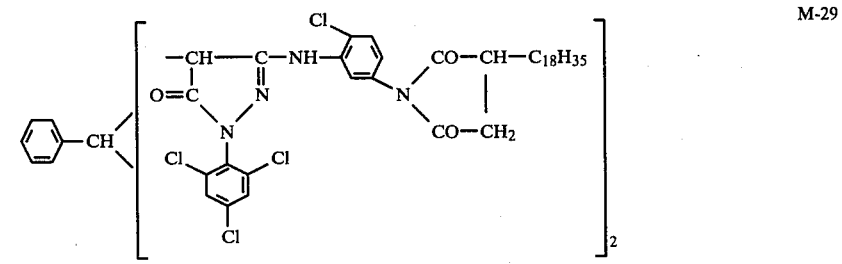 M-29
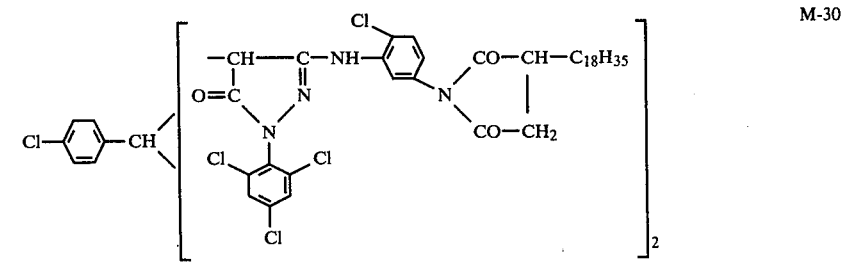 M-30
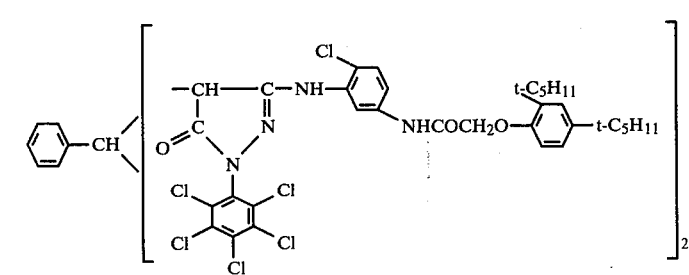 M-31

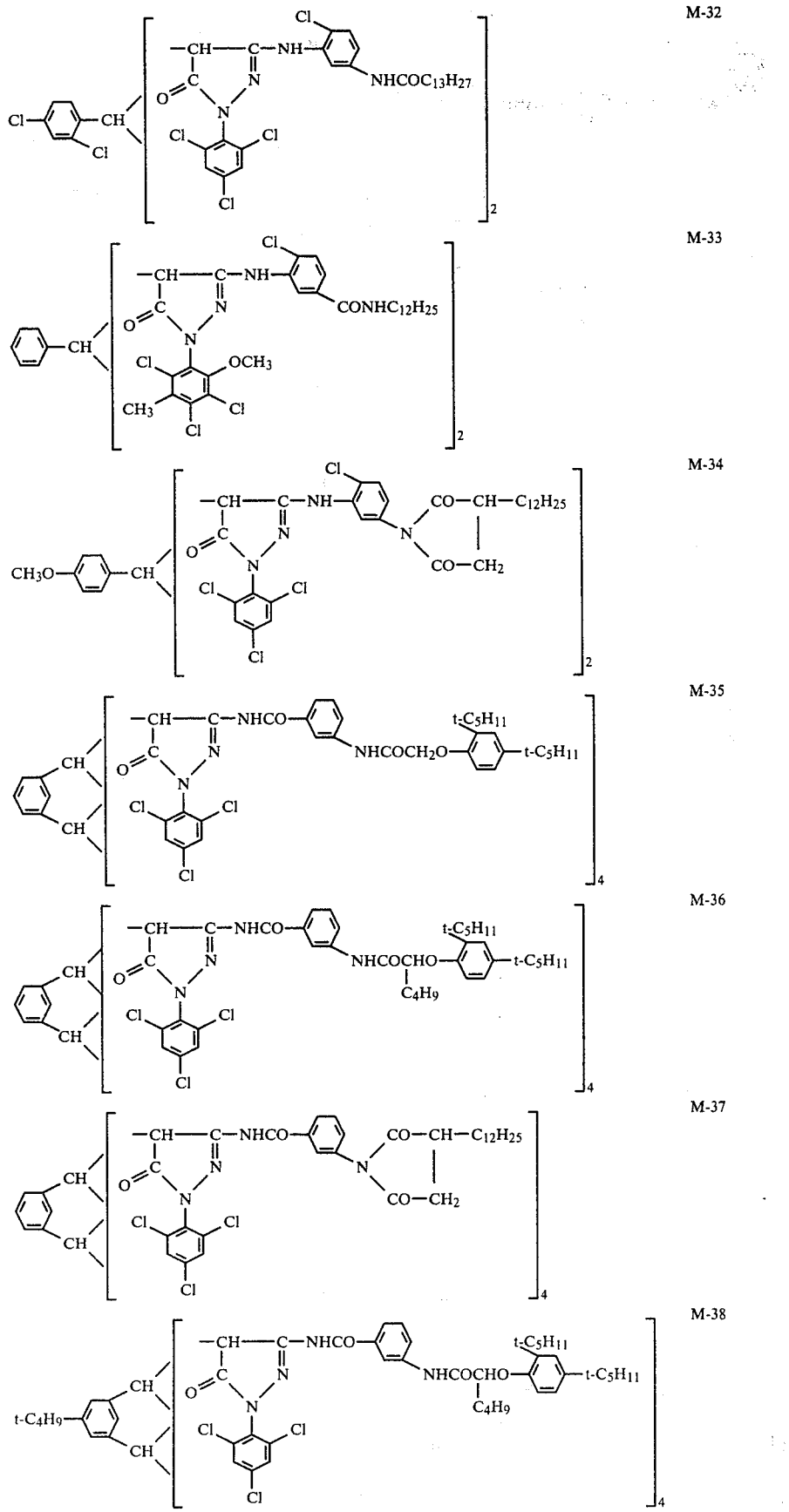

-continued

M-39, M-40, M-41, M-42, M-43 (chemical structures)

The magenta color formers used in the present invention, besides what have been enumerated hereinabove, include, e.g., U.S. Pat. Nos. 3,311,476, 3,419,391, 3,888,680 and 2,618,641, West German Patents OLS 2,015,814, 2,357,102 and 2,357,122, Japanese Patent L-O-P Publications 49-129538, 51-105820, 54-12555, 54-48540, 51-112342, 51-112343, 51-108842, 52-51939 and 52-58533, and Japanese Patent Application, wherein their synthetic methods are of course described.

Any of these magenta color formers may be incorporated into a silver halide emulsion layer singly or in a mixture of two or more kinds thereof, or otherwise in a mixture with one that is substituted at the active site thereof by arylazo, i.e., the so-called colored coupler as is described in U.S. Pat. No. 3,005,712. The quantity to be incorporated should be 1-25 mols per mol of a green-sensitive silver halide, the incorporation being made in an ordinary manner.

The oil-soluble photographic additives other than the couplers involved in the present invention are described below:

The DIR compounds, which become colorless coupling with the oxides of a color developing agent, used in the present invention include those which are described in, e.g., U.S. Pat. Nos. 3,632,345 and 3,928,041, Japanese Patent L-O-P Publications 49-77635, 49-104630, 50-36125, 50-15273, 51-6724, 52-23344 and 50-147716.

The anti-color stain agents used in the present invention, the compounds used for the prevention of the fog or stains frequently caused by the useless reaction between couplers and the oxides of developing agents oxidized by air, include those described in, e.g., U.S. Pat. Nos. 2,336,327, 2,360,290, 2,403,721, 2,701,197, 2,728,659 and 3,700,453, British Pat. No. 891,158.

The anti-light discoloration agents used in the present invention include those which are described in, e.g., U.S. Pat. Nos. 3,432,300 and 3,573,050, Japanese Patent Publications 49-20977, 48-31256 and 48-31625, Japanese Patent L-O-P Publications 53-17729 and 54-48538.

The ultraviolet ray absorbing agents used in the present invention include benztriazoles and benzophenone series comounds described in, e.g., U.S. Pat. Nos. 3,004,896, 3,253,921 and 3,705,805, Japanese Patent Publication 48-41572, Japanese Patent L-O-P Publication 50-25337.

The following are embodiments of the present invention.

EXAMPLE 1

A mixture comprising 5 g of an yellow coupler, Exemplified Compound (Y-2), 5 g of butyldiphenyl phosphate, the foregoing high boiling solvent, exemplified compound (2) and 10 g of ethyl acetate was dissolved by heating. The resulting liquid was added to 60 ml of a 5% aqueous gelatin solution containing 0.3 g of sodium dodecylbenzenesulfonate and emulsified and dispersed by means of a colloid mill. Then the coupler was uniformly finely dispersed together with the solvent, thus producing an emulsified and dispersed liquid. All the thus produced dispersed liquid was added to 200 g of a blue-sensitive silver chlorobromide emulsion containing photographic additives such as a hardener, coating aid, etc., and the resulting emulsion was coated on a polyethylene-coated baryta paper and dried, whereby Sample 1 was obtained.

In a similar manner to the above procedure with the exception that the high boiling solvents of the present invention, Exemplified Compounds (4) and (5) were used in place of the high boiling solvent, Exemplified compound (2) in the preceding procedure, whereby Samples 2 and 3 were obtained respectively. And as control samples, Samples 4 and 5 were prepared by the use of the same quantities of dibutyl phthalate (DBP) and tricresyl phosphate (TCP) in place of the high boiling solvent, Exemplified Compound (2) in the present invention.

Each of Samples 1 through 5 was given an exposure to light through the step wedge for sensitometry, and was then treated in the following processing steps:

| Color Developing Process (at 31° C.) | Processing Period |
| --- | --- |
| Color developing | 3 min. |
| Bleach-fixing | 1 min. |
| Washing | 2 min. |
| Stabilizing | 1 min. |
| Washing | 10 min. |
| Drying (not exceeding 95° C.) | |

The respective compositions of the processing solutions used in the steps are as follows:

| Color developing solution: | |
| --- | --- |
| N-ethyl-N-β-methanesulfonamide ethyl-3-methyl-4-aminoaniline sulfate | 4.0 g |
| Hydroxylamine | 2.0 g |
| Potassium carbonate | 25.0 g |
| Sodium chloride | 0.1 g |
| Sodium bromide | 0.2 g |
| Anhydrous sodium sulfite | 2.0 g |
| Benzyl alcohol | 10.0 ml |
| Polyethylene glycol (average degree of polymerization: 400) | 3 ml |
| Water to make 1 liter, whose pH is controlled 10.0 by sodium hydroxide | |
| Bleach-fixing solution: | |
| Iron-sodium ethylenediaminetetraacetate | 60.0 g |
| Ammonium thiosulfate | 100.0 g |
| Sodium hydrogensulfite | 10.0 g |
| Sodium metabisulfite | 3.0 g |
| Water to make 1 liter, whose pH is controlled 6.6 by aqueous ammonia | |
| Stabilizing solution: | |
| Succinic acid | 10.0 g |
| Formalin (37% aqueous solution) | 15.0 ml |
| Add 800 ml of water, then sodium acetate to make pH 3.9, and thereafter add water again to make 1 liter. | |

The resulting yellow image of each of the samples was measured on its density by the use of a densitometer (Model KD-7R, manufactured by Konishiroku Photo Ind. Co., Ltd.), and from the measurement were found the sensitivity, fog and maximum density (Dmax) of each sample. The results are shown in Table 1, wherein the sensitivity is given as relative sensitivity to that of Control Sample DBP regarded as 100.

TABLE 1

| Sample No. | High boiling solvent | Sensitivity | Fog | Dmax |
| --- | --- | --- | --- | --- |
| 1 | Exemplified Compound 2 | 123 | 0.07 | 2.95 |
| 2 | Exemplified Compound 4 | 108 | 0.08 | 2.83 |
| 3 | Exemplified Compound 5 | 115 | 0.07 | 2.85 |
| 4 | Control DBP | 100 | 0.07 | 2.75 |
| 5 | Control TCP | 98 | 0.08 | 2.70 |

From Table 1, Samples 1–3 with the high boiling solvents of the present invention dispersedly incorporated therein are found out to be better in the color formability than Control Samples 4 and 5. And, Samples 1–5 were tested for their resistance to light by use of a xenon fade-o-meter, wherein the samples were exposed to the lamp light over a period of eight days. The results are shown in Table 2, in which the values are given as dye residual degrees (%) at the portions of initial density of 1.0 and maximum density after the 8 days of treatment for testing the resistance to light.

TABLE 2

| Sample No. | High boiling solvent | Initial density (1.0): residual % | Initial density (Dm): residual % |
| --- | --- | --- | --- |
| 1 | Exemplified Compound 2 | 83 | 82 |
| 2 | Exemplified Compound 4 | 85 | 86 |
| 3 | Exemplified Compound 5 | 84 | 87 |
| 4 | Control DBP | 72 | 73 |
| 5 | Control TCP | 75 | 75 |

As obvious from Table 2, Samples 1–3 with the high boiling solvents of the present invention dispersedly incorporated therein are found out to be remarkably improved in the resistance to light as compared to Control Samples DBP and TCP.

EXAMPLE 2

Emulsified and dispersed liquids were prepared each of which has the following composition containing a cyan color former, Exemplified Compound C-26:

| Cyan coupler | 5 g |
| --- | --- |
| High boiling organic solvent | 5 g |

| | | |
|---|---|---|
| Ethyl acetate | 10 g | |
| Sodium dodecylbenzene-sulfonate | 0.3 g | |
| 5% aqueous gelatin solution | 60 ml | |

The cyan color former was added to each mixture of the respective high boiling solvents shown below with ethyl acetate and dissolved by heating to 70° C. The resulting each liquid was added to a 5% aqueous gelatin solution containing sodium dodecylbenzenesulfonate and the mixture was emulsified and dispersed by means of a colloid mill. The whole quantity of the thus obtained liquid was then added to 200 g of a red-sensitive silver chlorobromide emulsion containing photographic additives such as a hardener, coating aid, etc., and the emulsion was coated on a polyethylene-coated baryta paper and dried. The high boiling solvents used:

Exemplified Compounds (2) and (6)

Control Compound DBP

The resulting samples 6-8 were exposed to light and processed in the same manner as in Example 1, whereby color-developed samples were obtained. Two sets of these color-developed samples were stored over the period of two weeks in the dry air at the temperature of 77° C. and in the wet air at the temperature of 60° C. at 80% RH, to test the preservability of the dye image.

The results of the maximum densities imediately after the treatment, dye residual degrees (%), and discoloration to green are shown in Table 3, wherein the values of dye residual percent are the ones obtained at the initial density of 1.5 after the two weeks of treatment, while the values of discoloration to green are indicated in terms of the difference (after treatment B/R—Prior to treatment B/R) at D=1.5.

TABLE 3

| | | | 60° C./80% RH | | 77° C./Dry | |
|---|---|---|---|---|---|---|
| Sample No. | High boiling solvent | Dmax | Dye residual % | Discoloration to green | Dye residual % | Discoloration to green |
| 6 | Exemplified Compound 2 | 2.5 | 88 | 0.11 | 70 | 0.25 |
| 7 | Exemplified Compound 6 | 2.4 | 89 | 0.10 | 64 | 0.29 |
| 8 | Control DBP | 2.3 | 88 | 0.11 | 60 | 0.35 |

As obvious from Table 3, Samples 6 and 7, emulsified and dispersed with the use of the high boiling solvnets of the present invention are found out to be excellent in the color formability as compared to Control DBP, and significantly improved in the preservability of the color image treated in the dry air at 77° C.

EXAMPLE 3

Emulsified and dispersed liquids were prepared each having the following composition containing a magenta color former,

| Exemplified Compound M-6: | |
|---|---|
| Magenta coupler | 10 g |
| 1,4-dioctyloxy-2,5-dipentylbenzene* | 3 g |
| High boiling organic solvent | 10 g |
| Ethyl acetate | 20 g |

| Exemplified Compound M-6: | |
|---|---|
| Sodium dodecylbenzene-sulfonate | 0.3 g |
| 5% aqueous gelatin solution | 60 ml |

Note:
*Anti-photodiscoloration agent

The anti-photodiscoloration agent and magenta color former were added to each mixture of the respective high boiling solvents shown below with ethyl acetate and dissolved by heating to 70° C. The resulting solution was added to a 5% aqueous gelatin solution containing sodium dodecylbenzenesulfonate, and the mixture was emulsified and dispersed by means of a colloid mill. The whole quantity of the thus prepared liquid was added to 200 g of a green-sensitive silver chlorobromide emulsion containing photographic additives such as a hardener, coating aid, etc., and the thus prepared emulsion was coated on a polyethylene-coated baryta paper and dried. The high boiling solvents used:

Exemplified Compounds (1) and (4)

Control Compounds DBP and trioctyl phosphate (TOP)

The obtained samples 9-12 each was examined as to the presence of its repellence, and was exposed to light and processed in the same manner as in Example 1, thus producing a magenta color image. These processed samples were tested as to their resistance to light by use of a xenon fade-o-meter, in which the samples were exposed to the lamp light over the period of eight days, and also were examined as to degrees of their yellow stains appearing at the non-color forming portions thereof. The results are shown in Table 4, wherein the values of dye residual degrees representing the samples' resistance to light are the ones sought at the initial density of 1.5.

TABLE 4

| | | Resistance to light | | |
|---|---|---|---|---|
| Sample No. | High boiling solvent | Dye residual % | Yellow stain | Repellence |
| 9 | Exemplified Compound 1 | 80 | 0.16 | None |
| 10 | Exemplified Compound 4 | 82 | 0.15 | None |
| 11 | Control DBP | 78 | 0.25 | None |
| 12 | Control TOP | 82 | 0.24 | Present |

As seen from Table 4, it is understood that Samples 9 and 10 are more excellent in the resistance to light than Control DBP and have less yellow stains than Control TOP has, and also excellent in the uniformity of coating.

EXAMPLE 4

Emulsified and dispersed liquids were prepared each having the following composition containing a magenta color former,

| Exemplified Compound M-20: | |
|---|---|
| Magenta coupler | 10 g |
| 2-(1-phenyl-5-tetrazolylthio)-4-(2,4-di-tert-amylphenoxy-acetamide)-1-indanone* | 1 g |
| High boiling solvent | 10 g |
| Ethyl acetate | 20 g |
| Sodium dodecylbenzene- | |

-continued

| Exemplified Compound M-20: | |
|---|---|
| sulfonate | 0.3 g |
| 5% aqueous gelatin solution | 60 ml |

Note:
*DIR compound

The magenta color former and the DIR compound were added to each mixture of the respective high boiling organic solvents shown below with ethyl acetate and dissolved by heating to 70° C. The resulting solution was added to a 5% aqueous gelatin solution containing sodium dodecylbenzenesulfonate, and the mixture was emusified and dispersed by means of a colloid mill. The whole quantity of the thus prepared liquid was added to 200 g of a green-sensitive silver iodobromide emulsion containing photographic additives such as a hardener, coating aid, etc., and the emulsion was coated on a cellulose acetate film base and dried. The high boiling solvents used:

Exemplified Compounds (2), (4) and (8)

Control Compounds TCP and
N,N-diethyl-dodecaneamide (DELA)

The resulting samples 13–17 each was exposed to light in an ordinary manner and processed in accordance with the following color processing steps:

| Processing Steps (38° C.) | |
|---|---|
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |

The respective compositions of the processing solutions used in the above steps are as follows:

| Color developing solution: | |
|---|---|
| 4-amino-3-methyl-N-ethyl-N-(β-hydroxyethyl)-aniline sulfate | 4.75 g |
| Anhydrous sodium sulfite | 4.25 g |
| Hydroxyamine ½ sulfate | 2.0 g |
| Anhydrous potassium carbonate | 37.5 g |
| Sodium bromide | 1.3 g |
| Trisodium nitrilotriacetate, monohydrated | 2.5 g |
| Potassium hydroxide | 1.0 g |
| Water to make 1 liter, whose pH is controlled 10.0 by potassium hydroxide | |
| Bleaching solution: | |
| Iron-ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| Water to make 1 liter, whose pH is controlled 6.0 by adding aqueous ammonia | |
| Fixing solution: | |
| Ammonium thiosulfate (50% aqueous solution) | 152 ml |
| Anhydrous sodium sulfite | 12.4 g |
| Water to make 1 liter, whose pH is controlled 6.5 using acetic acid | |
| Stabilizing solution: | |
| Formalin (37% aqueous solution) | 5.0 ml |
| Koniducks (manufactured by Konishiroku Photo Ind. Co., Ltd.) | 7.5 ml |
| Water to make 1 liter | |

The density of the magenta image of each sample obtained by the above processings was measured by the use of a densitometer (Model KD-7R, manufactured by Konishiroku Photo Ind. Co., Ltd.) thereby to find the sensitivity, fog and D max of each of the samples. In addition, the sensitivity was given as a relative value to that of Control TCP regarded as 100.

On the other hand, in order to examine the change of the dye forming degree by the magenta color former in the foregoing processings, the samples whose densities have already been measured were immersed in a red prussiate bleaching bath for 5 minutes at 20° C., then washed and dried, and the thus treated samples were measured again on their densities. The dye forming degrees were expressed in the values of 100× (the value of Dmax in ordinary development ÷ the value of Dmax after the red prussiate treatment). The results are shown in Table 5.

The red prussiate bleaching bath has the following composition:

| $K_3Fe(CN)_6$ | 95 g |
|---|---|
| $K_4Fe(CN)_6$ | 65 g |
| Nitrotriacetate | 18 g |
| KBr | 25 g |
| Water to make 1 liter | |

TABLE 5

| Sample No. | High boiling solvent | Sensitivity | Fog | Dmax | Dye forming degree (%) |
|---|---|---|---|---|---|
| 13 | Exemplified Compound 2 | 121 | 0.11 | 2.18 | 94 |
| 14 | Exemplified Compound 4 | 125 | 0.14 | 2.20 | 94 |
| 15 | Exemplified Compound 8 | 122 | 0.12 | 2.18 | 96 |
| 16 | Control TCP | 100 | 0.11 | 1.68 | 78 |
| 17 | Control DELA | 120 | 0.25 | 2.18 | 92 |

As seen from Table 5, Samples 13–15 which applied the high boiling organic solvents of the present invention show significantly higher sensitivities, maximum densities and dye forming degrees than those of Control Samples TCP and DELA, and also show excellent processing stabilities.

Meanwhile, the coated, unexposed samples 13–17 were allowed to stand over a period of three months in the air conditioned at the temperature of 25° C. with 60% relative humidity, and thereafter were processed in such an ordinary manner as in above. The resulting samples were compared to the ones obtained by processing upon coating thereby to examine the preservability of the samples as raw stocks. The results are shown in Table 6.

TABLE 6

| | | Sensitivity | | Dmax | |
|---|---|---|---|---|---|
| Sample No. | High boiling silvent | Upon coating | 3-month standing | Upon coating | 3-month standing |
| 13 | Exemplified Compound 2 | 121 | 114 | 2.18 | 2.08 |
| 14 | Exemplified Compound 4 | 125 | 118 | 2.20 | 2.07 |
| 15 | Exemplified Compound 8 | 122 | 115 | 2.18 | 2.10 |

TABLE 6-continued

| Sample No. | High boiling silvent | Sensitivity Upon coating | Sensitivity 3-month standing | Dmax Upon coating | Dmax 3-month standing |
|---|---|---|---|---|---|
| 16 | Control TCP | 100 | 97 | 1.68 | 1.60 |
| 17 | Control DELA | 120 | 50 | 2.18 | 1.12 |

As apparent from Table 6, it is understood that Samples 13–17 prepared using the high boiling solvents of the present invention for the magenta color former involved in the present invention are highly improved in the preservability thereof as raw stocks as compared to Control DELA.

EXAMPLE 5

Coated Samples 17–21 were prepared by emulsifying and dispersing, in the same composition and in the same manner as in Example 4, a magenta color former, Exemplified Coupler M-40 of the present invention, high boiling solvents, Exemplified Compounds (2), (5) and (10) of the present invention, and Compounds TCP and DBP as control high boiling solvents. The resulting samples each was exposed to light and processed in the same manner as in Example 4 to examine its sensitivity, fog and D max. The results are shown in Table 7, wherein the values of sensitivities are indicated relative to that of Control TCP regarded as 100.

TABLE 7

| Sample No. | High boiling solvent | Sensitivity | Fog | Dmax |
|---|---|---|---|---|
| 17 | Exemplified Compound 2 | 140 | 0.08 | 2.56 |
| 18 | Exemplified Compound 5 | 135 | 0.08 | 3.10 |
| 19 | Exemplified Compound 10 | 132 | 0.07 | 2.38 |
| 20 | Control TCP | 100 | 0.07 | 1.53 |
| 21 | Control DBP | 98 | 0.08 | 1.55 |

From Table 7, it is understood that Samples 17–19 prepared with the use of the high boiling solvents of the present invention for the multi-pyrazolone type magenta coupler involved in the present invention are significantly improved in the color formability as compared to the conventional high boiling solvents, Control Samples 20 and 21.

EXAMPLE 6

The same test was practised as mentioned in the Example 4 except that the magenta coupler M-36, high boiling solvents described in the Table 8 were employed in place of M-20 and high boiling solvent described in the Table 4, respectively, to obtain the Table 8, wherein the sensitivity was given as relative value to that of control Sample regarded as 100.

TABLE 8

| Sample No. | High boiling solvent | Sensitivity | Fog | Dmax |
|---|---|---|---|---|
| 22 | Exemplified Compound 2 | 135 | 0.07 | 2.86 |
| 23 | Exemplified Compound 5 | 140 | 0.07 | 2.72 |
| 24 | Exemplified Compound 6 | 132 | 0.08 | 2.63 |
| 25 | Control TCP | 100 | 0.08 | 1.75 |

As it is apparent from the Table 8, samples employing high boiling solvent of the present invention provide excellent high density of magenta dye comparing with the sample using a conventional high boiling solvent.

What is claimed is:

1. A silver halide photographic material containing a hydrophobic photographic additive being contained in oil particles dispersed in a hydrophilic colloidal layer coated on a support wherein the oil particles consist of a compound represented by a formula

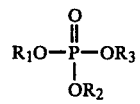

wherein $R_1$ represents an alkyl radical, and each of $R_2$ and $R_3$ represents an aryl radical, said additive comprising a magenta dye-forming coupler.

* * * * *